United States Patent
Cai et al.

(10) Patent No.: US 12,364,410 B2
(45) Date of Patent: Jul. 22, 2025

(54) REAL-TIME ULTRA-QUALITY MULTI-PARAMETRIC FOUR-DIMENSIONAL MAGNETIC RESONANCE IMAGING SYSTEM AND THE METHOD THEREOF

(71) Applicant: THE HONG KONG POLYTECHNIC UNIVERSITY, Hong Kong (CN)

(72) Inventors: Jing Cai, Hong Kong (CN); Haonan Xiao, Hong Kong (CN); Tian Li, Hong Kong (CN)

(73) Assignee: THE HONG KONG POLYTECHNIC UNIVERSITY, Hong Kong (CN)

(*) Notice: Subject to any disclaimer, the term of this patent is extended or adjusted under 35 U.S.C. 154(b) by 132 days.

(21) Appl. No.: 18/163,913

(22) Filed: Feb. 3, 2023

(65) Prior Publication Data
US 2024/0260848 A1    Aug. 8, 2024

(51) Int. Cl.
*A61B 5/055* (2006.01)
*G01R 33/48* (2006.01)
(Continued)

(52) U.S. Cl.
CPC .......... *A61B 5/055* (2013.01); *G01R 33/4826* (2013.01); *G01R 33/5608* (2013.01);
(Continued)

(58) Field of Classification Search
CPC ................ A61B 5/055; G01R 33/4826; G01R 33/5608; G01R 33/56509; G06T 7/0012; G06T 2207/10088; G06T 2207/20081
See application file for complete search history.

(56) References Cited

U.S. PATENT DOCUMENTS

2023/0342886 A1* 10/2023 Meyer ...................... G06T 5/70
2024/0249395 A1*  7/2024 Datta .................. G06N 3/0475

OTHER PUBLICATIONS

Shao, Hua-Chieh, et al. "Real-time MRI motion estimation through an unsupervised k-space-driven deformable registration network (KS-RegNet)." Physics in Medicine & Biology 67.13 (2022): 135012. (Year: 2022).*

(Continued)

*Primary Examiner* — Rishi R Patel
(74) *Attorney, Agent, or Firm* — S&F/WEHRW

(57) ABSTRACT

A computer-implemented method for training a convolutional neural network (CNN) using training data comprising a pair of original and downsampled 4D magnetic resonance imaging (MRI) data is provided. The CNN is used to generate multi-parametric 4D magnetic resonance (MR) images based on multi-parametric 3D MR images in real-time. The method includes receiving a 4D MR image formed by a plurality of fixed images of different frames; converting the plurality of fixed images into a plurality of k-space data by non-uniform fast Fourier transform (NUFFT); applying radial scan to the k-space data to simulate real-time MR image acquisition, and generating a plurality of downsampled fixed images by inverse NUFFT; training a CNN with training data comprising the 4D MR image and the corresponding downsampled 4D MR image; and estimating the multi-parametric 4D MR image in real-time by applying apply the predicted DVF to the multi-parametric 3D MR images.

17 Claims, 9 Drawing Sheets

(51) Int. Cl.
  *G01R 33/56* (2006.01)
  *G01R 33/565* (2006.01)
  *G06T 7/00* (2017.01)
(52) U.S. Cl.
  CPC ...... *G01R 33/56509* (2013.01); *G06T 7/0012* (2013.01); *G06T 2207/10088* (2013.01); *G06T 2207/20081* (2013.01)

(56) References Cited

OTHER PUBLICATIONS

Xiao, Haonan, et al. "A dual-supervised deformation estimation model (DDEM) for constructing ultra-quality 4D-MRI based on a commercial low-quality 4D-MRI for liver cancer radiation therapy." Medical physics 49.5 (2022): 3159-3170. (Year: 2022).*

Xiao, Haonan, et al. "Real-time High-quality Multi-parametric 4D-MRI Using Deep Learning-based Motion Estimation from Ultra-undersampled Radial K-space." (Year: 2022).*

Li G, Wei J, Kadbi M, et al. Novel Super-Resolution Approach to Time-Resolved Volumetric 4-Dimensional Magnetic Resonance Imaging With High Spatiotemporal Resolution for Multi-Breathing Cycle Motion Assessment. International journal of radiation oncology, biology, physics. 2017;98(2):454-462. doi:10.1016/j.ijrobp.2017.02.016.

Freedman JN, Collins DJ, Gurney-Champion OJ, et al. Super-resolution T2-weighted 4D MRI for image guided radiotherapy. Radiother Oncol. Dec. 2018; 129(3):486-493. doi:10.1016/j.radonc.2018.05.015.

Zhang L, Yin FF, Li T, et al. Multi-contrast four-dimensional magnetic resonance imaging (MC-4D-MRI): Development and initial evaluation in liver tumor patients. Med Phys. Dec. 2021;48(12):7984-7997. doi:10. 1002/mp.15314.

Huang G, Liu Z, Van Der Maaten L, Weinberger KQ. Densely connected convolutional networks. 2017:4700-4708.

Balakrishnan G, Zhao A, Sabuncu MR, Guttag J, Dalca AV. VoxelMorph: a learning framework for deformable medical image registration. IEEE Trans Med Imaging. Feb. 4, 2019;doi:10.1109/TMI.2019.2897538.

Nie X, Huang K, Deasy J, Rimner A, Li G. Enhanced super-resolution reconstruction of T1w time-resolved 4DMRI in low-contrast tissue using 2-step hybrid deformable image registration. J Appl Clin Med Phys. Oct. 2020;21(10):25-39. doi:10.1002/acm2.12988.

Nie X, Saleh Z, Kadbi M, et al. A super-resolution framework for the reconstruction of T2-weighted (T2w) time-resolved (TR) 4DMRI using T1w TR-4DMRI as the guidance. Med Phys. Jul. 2020;47(7):3091-3102. doi:10.1002/mp.14136.

Li G, Sun A, Nie X, et al. Introduction of a pseudo demons force to enhance deformation range for robust reconstruction of super-resolution time-resolved 4DMRI. Med Phys. Nov. 2018;45(11):5197-5207. doi:10.1002/mp.13179.

Xiao H, Han X, Zhi S, et al. Ultra-Quality Multi-Parametric 4D-MRI for Real-Time Tumor Tracking in Liver Radiation Therapy Using A Dual-Supervised Downsampling-Invariant Deformable Registration Model. Wiley 111 River St, Hoboken 07030-5774, NJ USA; 2022:E151-E151.

* cited by examiner

| MRI Type | CNR | PBM | Lung-liver edge FWHM (mm) | | Motion Error (mm) | | |
|---|---|---|---|---|---|---|---|
| | | | In-plane | Cross-plane | SI | AP | ML |
| Original 4D-MRI | 8.30±6.87 | 0.70±0.01 | 6.7±2.9 | 8.7±6.4 | N/A | N/A | N/A |
| UQ T1w 4D-MRI | 8.66±6.46 | 0.38±0.01 | 4.7±2.4 | 8.9±3.7 | 1.12±0.89 | 0.51±0.39 | 0.41±0.31 |
| UQ T2w 4D-MRI | 22.49±21.54 | 0.40±0.01 | 3.1±1.3 | 5.8±2.5 | 1.24±0.93 | 0.55±0.39 | 0.45±0.38 |
| UQ 4D-DWI (b=50) | 35.28±35.29 | 0.55±0.01 | 6.4±4.5 | 5.2±2.4 | 1.21±0.86 | 0.51±0.37 | 0.42±0.32 |
| UQ 4D-DWI (b=800) | 29.81±24.36 | 0.61±0.02 | 4.5±1.4 | 9.4±6.9 | 1.15±0.82 | 0.52±0.38 | 0.38±0.28 |

FIG. 9

REAL-TIME ULTRA-QUALITY MULTI-PARAMETRIC FOUR-DIMENSIONAL MAGNETIC RESONANCE IMAGING SYSTEM AND THE METHOD THEREOF

FIELD OF THE INVENTION

The present invention is generally related to magnetic resonance imaging (MM) system and method. Particularly, the present disclosure is related to a system and a method for generating real-time ultra-quality multi-parametric four-dimensional (4D) magnetic resonance (MR) images.

PRIOR DISCLOSURES BY THE INVENTORS OR A JOINT INVENTOR

Part of the present invention was disclosed in Medical Physics Vol. 49. No. 6. (Xiao, H., et al. "Ultra-Quality Multi-Parametric 4D-MRI for Real-Time Tumor Tracking in Liver Radiation Therapy Using a Dual-Supervised Downsampling-Invariant Deformable Registration Model." MEDICAL PHYSICS. Vol. 49. No. 6. 111 RIVER ST, HOBOKEN 07030-5774, NJ USA: WILEY, 2022.) on Jun. 1, 2022. Part of the present invention was also disclosed in the American Association of Physicists in Medicine (AAPM) Annual Meeting & Exhibition on Jul. 10, 2022. Both disclosures are grace period inventor-originated disclosures disclosed within one year before the effective filing date of this application.

BACKGROUND OF THE INVENTION

MRI is widely used in medical imaging applications for non-invasively imaging of a body part using the magnetization properties of atomic nuclei. During an MRI imaging procedure, an external magnetic field and a radio frequency signal of Larmor frequency are employed to a region, such as an internal body part, to obtain an image of the internal biological structures. Typically, the region to be imaged is scanned by a sequence of measurement cycles to receive magnetic resonance signals as generated from the excitation. The magnetic resonance signals are digitized and processed to reconstruct the image. One important application of MRI is to image a human liver for medical diagnosis and detection of possible tumors in the liver. The development of the present invention is motivated by the difficulties encountered when performing real-time tumor tracking in liver radiation therapy.

4D MRI technology was introduced to include the time domain to the three spatial directions, which is a three-dimensional (3D) time-resolved phase-contrast MRI. The traditional 4D MRI technology is based on two-dimensional (2D) or 3D acquisition followed by the phase ordering of the acquired images using a computer program. Even with the reflecting respiratory movement, the 4D MRI can still present excellent soft tissue contrast, which is beneficial to respiratory movement management and target delineation in radiotherapy.

Li et al. [1] proposed to use the deformation vector field and high-quality 3D MR images for generating the 4D MR images, which can extract a deformation vector field from a low-resolution T1-weighted (T1w) 4D MRI and apply the deformation vector field to a high-resolution T1-weighted 3D MRI to obtain a high-resolution 4D MRI.

Freedman et al. [2] and Zhang et al. [3] extended the method of Li to T2-weighted (T2w) MR images and synthetic image contrasts. The development is focused on improving the motion accuracy and contrast diversity of this technique. However, the foregoing mentioned methods have some common shortcomings, making them unable to achieve real-time ultra-high-quality multi-parametric 4D MRI.

First, it is needed to spend a long time on image acquisition to meet the sampling conditions, which causes the image acquisition time being too long. Second, the reconstruction of the acquired images is executed offline, and it is unlikely to achieve real-time generation of the 4D MR images. In particular, the extraction of the deformation vector field is performed using traditional iterative optimization deformation registration algorithm, which usually requires processing time ranging from tens of minutes to several hours. In certain cases, the patient's irregular breathing cycles may cause respiratory motion artifacts and images imprecision. Furthermore, the image contrast agent may also be insufficient, and may need to use special software and/or hardware that cannot be provided clinically. Therefore, the current 4D MRI suffers from poor image quality, severe motion artifacts, long acquisition time, and incapable in performing real-time tracking. In summary, the above discussed shortcomings make the existing methods unable to provide high temporal resolution and real-time 4D MR images.

Accordingly, there is a need in the art to have a clinically available 4D MRI system and the method thereof with higher temporal resolution, better phase contrast, and higher image quality. Furthermore, other desirable features and characteristics will become apparent from the subsequent detailed description and the appended claims, taken in conjunction with the accompanying drawings and this background of the disclosure.

SUMMARY OF THE INVENTION

Provided herein is a 4D MRI system and a computer-implemented method for generating ultra-quality multi-parametric 4D MR images based on multi-parametric 3D MR images in real-time. The system is implemented using deep learning-based joint MR image reconstruction and motion estimation model for generating the ultra-quality multi-parametric 4D MR image.

According to the first aspect of the present disclosure, a computer-implemented method for training a convolutional neural network (CNN) using training data including a pair of original and downsampled 4D magnetic resonance imaging (MRI) data is provided. The CNN is used to generate multi-parametric 4D magnetic resonance (MR) images based on multi-parametric 3D MR images in real-time. The multi-parametric 4D MR images have an improved tumor contrast-to-noise ratio (CNR), an improved organ edges sharpness, and a reduced perceptual blur metric (PBM). The method includes receiving, by a processor, a 4D MR image formed by a plurality of fixed images of different frames; converting, by the processor, the plurality of fixed images into a plurality of k-space data by non-uniform fast Fourier transform (NUFFT); applying, by the processor, radial sampling to the k-space data to simulate real-time MR image acquisition; and generating a plurality of downsampled fixed images by inverse NUFFT (iNUFFT) for reconstructing a corresponding downsampled 4D MR image; training, by a machine learning method, a CNN with training data comprising the 4D MR image and the corresponding downsampled 4D MR image; and estimating, by the processor, the multi-parametric 4D MR image in real-time. The plurality of k-space data is an array of numbers representing spatial frequencies of the plurality of fixed images in a Cartesian coordinate system. The CNN is trained to calculate a predicted displacement vector field (DVF). The multi-parametric 4D MR image is estimated by applying apply the predicted DVF to the multi-parametric 3D MR images.

In certain embodiments, the method further includes dually supervising the step of training the CNN by an end-to-end point error (EPE) and a normalized correlation coefficient (NCC).

In certain embodiments, the method further includes generating a reference DVF from the 4D MR image using conventional registration methods as a ground truth DVF. The conventional registration methods include a parametric total variation (pTV) algorithm.

In certain embodiments, the step of dually supervising the step of training the CNN further includes determining a first loss function between the reference DVF and the predicted DVF as the EPE; and determining a second loss function between a warped image and the 4D MR image as the NCC.

In certain embodiments, the step of training the CNN includes reconstructing, by the reconstruction branch using a densely connected network, the plurality of downsampled fixed images to obtain reconstructed fixed images; and deformably registering, by the registration branch, the reconstructed fixed image and the 4D MR image to predict deformations between the reconstructed fixed image and the 4D MR image for determining the predicted DVF.

In certain embodiments, the step of deformably registering the reconstructed fixed image and the 4D MR image further includes pairing and mapping the reconstructed fixed image and the 4D MR image to a DVF pair for alignment.

In certain embodiments, the multi-parametric 3D MR images include T1-weighted (T1w) MRI, T2-weighted (T2w) MRI, and diffusion-weighted MR imaging (DWI).

According to the second aspect of the present disclosure, a 4D MM system is provided. The ultra-quality multi-parametric 4D MR image obtained from the present invention shows an improved tumor CNR, an improved organ edges sharpness, and a reduced PBM. The system includes one or more computer devices collectively programmed with a data pre-processing module, a model training module, and an image generating module. The data pre-processing module is configured to downsample a 4D MR image by NUFFT and generates a corresponding downsampled 4D MR image. The model training module for training a CNN with training data using a machine learning method, wherein the CNN is trained to calculate a predicted DVF. The image generation module is configured to apply the predicted DVF to the multi-parametric 3D MR images to estimate the multi-parametric 4D MR image from the multi-parametric 3D MR images in real-time. The training data for the CNN comprises the 4D MR image and the corresponding downsampled 4D MR image from the data pre-processing module. The model training module is dually supervised by an EPE and an NCC. The model training module is configured to perform deformation registration of the corresponding downsampled 4D MR image to train the CNN.

In certain embodiments, the 4D MR image is a moving image formed by a plurality of fixed images. The plurality of fixed images are converted into a plurality of k-space data in a Cartesian coordinate system by NUFFT.

In certain embodiments, the plurality of k-space data is transformed to real space to obtain a plurality of downsampled fixed images for training the CNN by iNUFFT. The corresponding downsampled 4D MR image comprises the plurality of downsampled fixed images.

In certain embodiments, the CNN is a dual-supervised downsampling-invariant deformable registration (D3R) model including a reconstruction branch and a registration branch.

In certain embodiments, the reconstruction branch is configured to reconstruct the plurality of downsampled fixed images using a densely connected network to obtain reconstructed fixed images. The densely connected network comprises a plurality of layers each having a dense block and a transition layer. An individual layer receives inputs from outputs of all previous layers of the plurality of layers.

In certain embodiments, the transition layer is configured to perform convolution and pooling. The densely connected network is characterized with a feed-forward characteristic for enhancing image details and suppressing artifacts.

In certain embodiments, the registration branch receives the reconstructed fixed images and the 4D MR image for predicting deformations between the reconstructed fixed images and the 4D MR image, thereby the registration branch generates the predicted DVF for the image generation module.

In certain embodiments, the registration branch is a supervised registration framework based on the CNN. The reconstructed fixed images and the 4D MR image are paired and mapped to a DVF pair for alignment.

In certain embodiments, the EPE determines a first loss function between a reference DVF and the predicted DVF. The NCC determines a second loss function between a warped image and the 4D MR image.

In certain embodiments, the reference DVF is a ground truth DVF computed from the 4D MR image using conventional registration methods for supervising the model training module. The conventional registration methods comprise a parametric total variation (pTV) algorithm.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects and advantages of the present invention are disclosed as illustrated by the embodiments hereinafter.

BRIEF DESCRIPTION OF THE DRAWINGS

The appended drawings contain figures to further illustrate and clarify the above and other aspects, advantages, and features of the present disclosure. It will be appreciated that these drawings depict only certain embodiments of the present disclosure and are not intended to limit its scope. It will also be appreciated that these drawings are illustrated for simplicity and clarity and have not necessarily been depicted to scale. The present disclosure will now be described and explained with additional specificity and detail through the use of the accompanying drawings in which:

FIG. 9 shows a table summarizing further statistical results from 31 patients with liver tumor for demonstrating the performance of the real-time 4D MRI system.

DETAILED DESCRIPTION OF THE INVENTION

Figure 1:
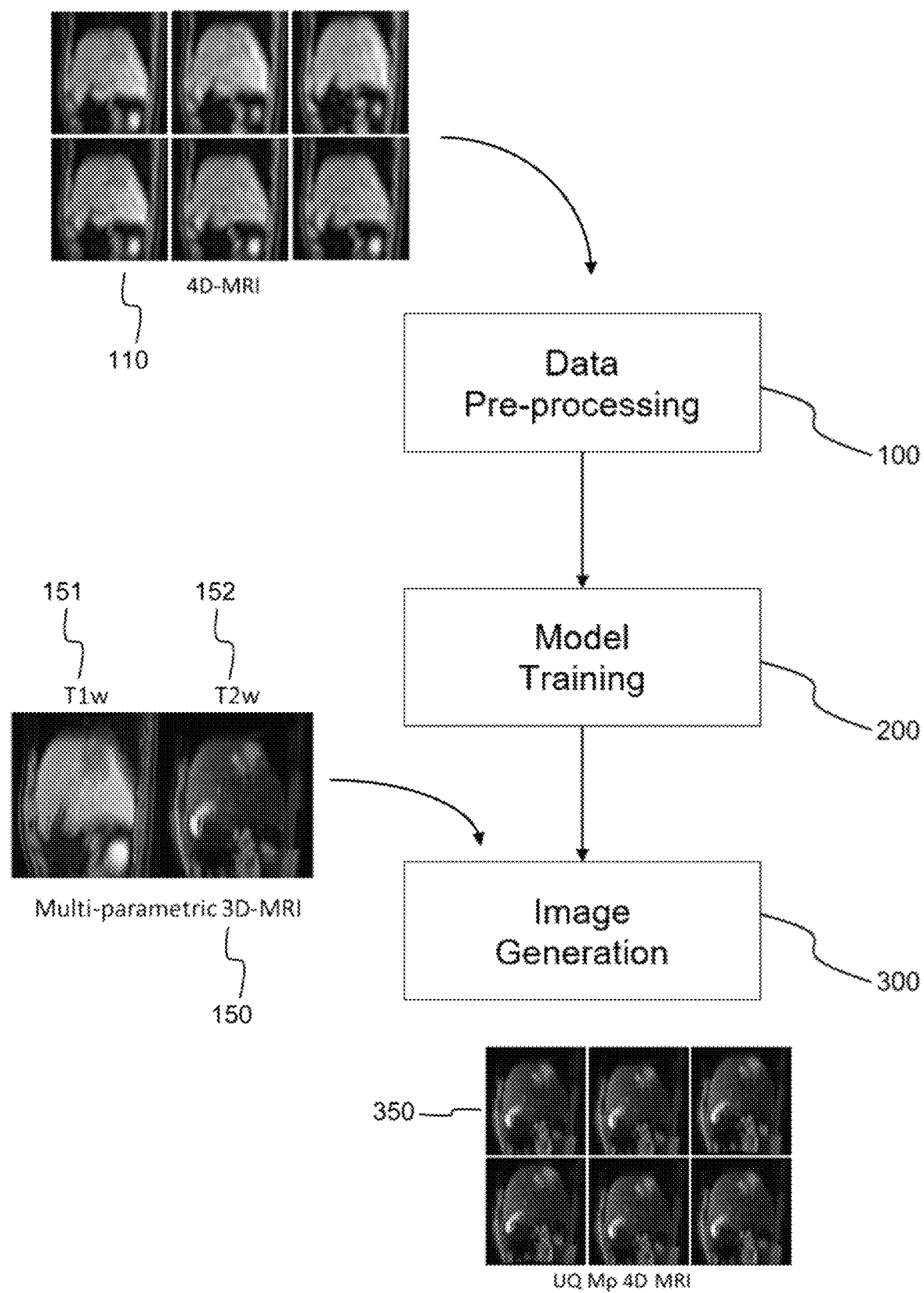
FIG. 1 shows a block diagram of the real-time 4D MRI system in accordance with certain embodiments of the present disclosure.

The following detailed description is merely exemplary in nature and is not intended to limit the disclosure or its application and/or uses. It should be appreciated that a vast number of variations exist. The detailed description will enable those of ordinary skilled in the art to implement an exemplary embodiment of the present disclosure without undue experimentation, and it is understood that various changes or modifications may be made in the function and structure described in the exemplary embodiment without departing from the scope of the present disclosure as set forth in the appended claims.

The benefits, advantages, solutions to problems, and any element(s) that may cause any benefit, advantage, or solution to occur or become more pronounced are not to be construed as a critical, required, or essential features or elements of any or all of the claims. The invention is defined solely by the appended claims including any amendments made during the pendency of this application and all equivalents of those claims as issued.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The terms "comprising," "having," and "including" or any other variation thereof, are to be construed as open-ended terms (i.e., meaning "including, but not limited to,") unless otherwise noted. The use of any and all examples, or exemplary language (e.g., "such as") provided herein, is intended merely to illuminate the invention better and does not pose a limitation on the scope of the invention unless otherwise claimed. No language in the specification should be construed as indicating any non-claimed element as essential to the practice of the invention. Further, unless expressly stated to the contrary, "or" refers to an inclusive "or" and not to an exclusive "or". For example, a condition A or B is satisfied by any one of the following: A is true and B is false, A is false and B is true, and both A and B are true. Terms of approximation, such as "about", "generally", "approximately", and "substantially" include values within ten percent greater or less than the stated value.

Unless otherwise defined, all terms (including technical and scientific terms) used in the embodiments of the present invention have the same meaning as commonly understood by an ordinary skilled person in the art to which the present invention belongs.

In certain embodiments, a method for generating real-time ultra-quality multi-parametric 4D MR image is disclosed. The method of the present disclosure is characterized in that the 4D MR images are determined using a convolutional neural network (CNN) for image reconstruction and deformable registration. In particular, the CNN provided is configured to extract the 4D displacement vector field (DVF) from the downsampled 4D MRI, which can enable real-time ultra-quality multi-parametric 4D MRI.

The 4D MM is favorable for image guidance for radiotherapy because it provides versatile image contrasts and complete 3D motion information, which is essential for cancer treatments. With the technological development of a real-time 4D MRI, the image guidance can be integrated with the radiotherapy treatment to improve the precision and the safety to the patient. Therefore, it is also apparent that the method of the present disclosure can be used to assist various invasive medical procedures to implement a real-time 4D magnetic resonance guided radiotherapy delivery system or other real-time 4D magnetic resonance guided treatment systems. In particular, the present invention can be applied to perform real-time tumor tracking in radiotherapy on a magnetic resonance linear accelerator (MR-Linac).

As it has been explained above, the existing real-time 4D MM may have the deficiencies of low image quality or low temporal resolution. Particularly for tumor tracking in liver, the presently available solutions require motion modeling, which need individual modeling for each patient and strong assumptions in implementation, such as consistent breathing pattern and anatomy. Therefore, the present invention is proposed to develop a real-time ultra-quality multi-parametric (UQ Mp) 4D MRI method using deep learning-based joint MR image reconstruction and motion estimation model for generating the 4D MR images.

FIG. 1 shows a block diagram of the real-time 4D MRI system (hereinafter referred to as the "system") comprising one or more computers collectively programmed with a data pre-processing module 100, a model training module 200, and an image generation module 300. The system is clinically available and may be integrated in a medical imaging device (such as an MRI apparatus) or separately provided as a medical image processing device. Therefore, the data pre-processing module 100, the model training module 200, and the image generation module 300 are software implemented modules implemented and programmed in one or more computer devices collectively to execute a computer-implemented method (hereinafter referred to as the "method") for generating multi-parametric 4D MR images 350 in real-time. In certain embodiments, the one or more computer devices may include a stand-alone computer device and a cloud-based computer platform. The system is provided with a deep learning-based joint MR image reconstruction and motion estimation model. The model is trained in the model training module 200 by using the training data from the data pre-processing module 100. The image generation module 300 receives multi-parametric 3D MR Image 150 to generate the multi-parametric 4D MR images 350. In particular, the multi-parametric 3D MR Image 150 may include, but not limited to, T1w MRI 151, T2-weighted (T2w) MRI 152, and diffusion-weighted MR imaging (DWI) with b-value of 50 and 800.

Figure 2:
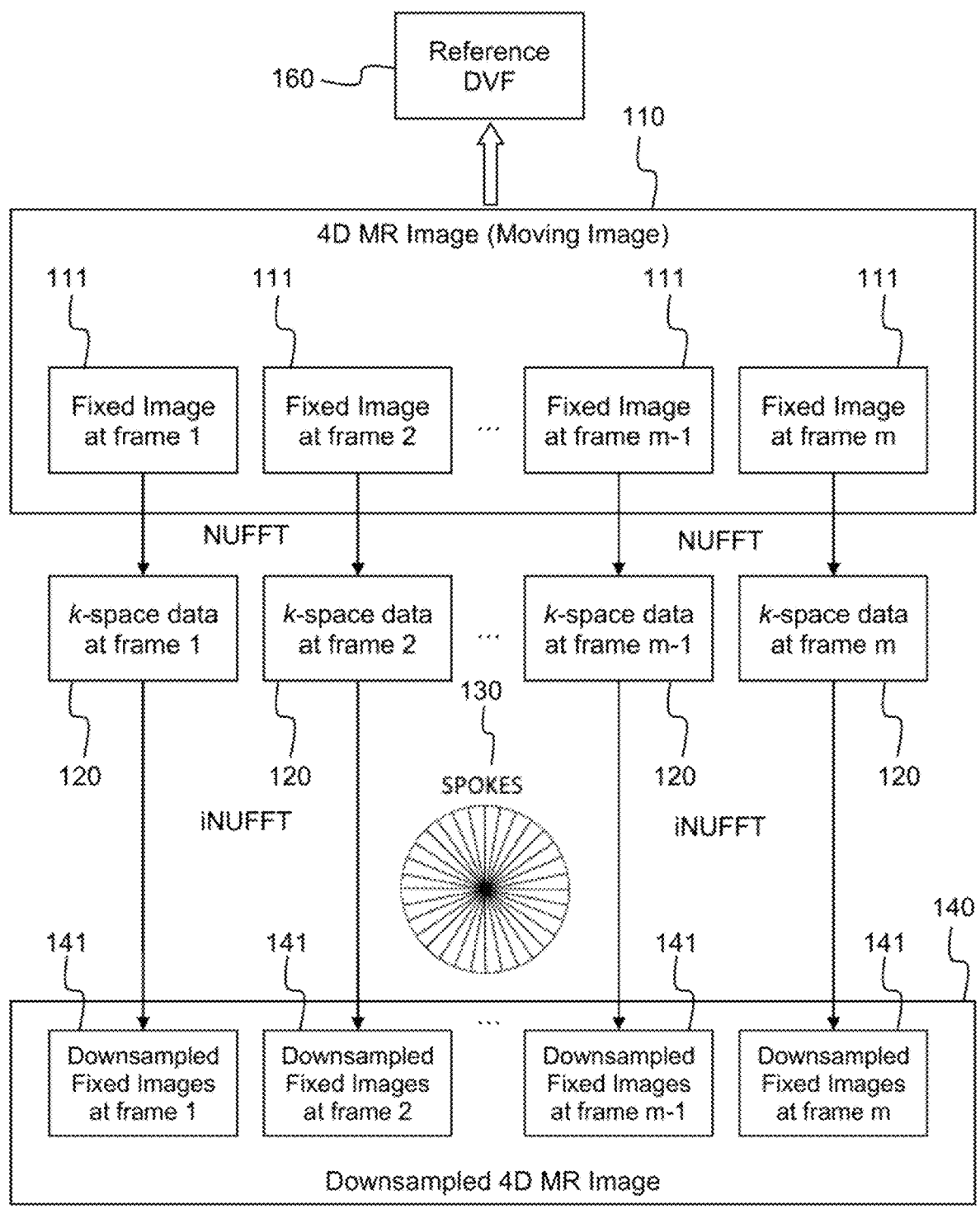
FIG. 2 shows a block diagram of the data pre-processing module in accordance with certain embodiments of the present disclosure.

FIG. 2 shows a block diagram of the data pre-processing module 100 in accordance with certain embodiments of the present disclosure. The data pre-processing module 100 is configured to use a processor or one or more computer devices to downsample the 4D MR image 110 and generate a corresponding downsampled 4D MR image 140 for simulating the limited image acquisition time in real-time MRI. The 4D MR image 110 may be collected clinically from the hospital or other medical institutes and received by the processor for pre-processing. The 4D MR image 110 is a moving image, which is formed by a plurality of fixed images 111 of different frames, wherein the plurality of fixed images 111 are high quality multi-parametric images, which may be 3D MR images or 2D MR images. In certain embodiments, the fixed images 111 are designated by frames 1, 2, . . . , m-1, m. The plurality of fixed images 111 are converted into a plurality of k-space data 120 at different frames by non-uniform fast Fourier transform (NUFFT), wherein the plurality of k-space data 120 is an array of numbers representing the spatial frequencies of the plurality of fixed images 111 in a Cartesian coordinate system. Therefore, the NUFFT is applied to downsample the 4D MR image 110.

In order to simulate real-time MR image acquisition using MRI, radial scan is applied by a processor to the k-space data 120 of the 4D MR image 110. In certain embodiments, n radial spokes 130 are collected from the k-space data 120 using 3D radial sampling. One critical problem with the existing solution is related to the motion artifacts. For the realization of real-time acquisition, the delay from the occurrence of the patient's action to the treatment response should be minimized, preferably to less than 500 ms. Meanwhile, the data lost should be reduced. The inventors of the present application have simulated the online acquisition in real-time tumor tracking using 100 as n, so 100 radial spokes 130 are collected. Inverse NUFFT (iNUFFT) is used to transform the simulated real-time image acquisition of the k-space data 120 back to the real space to obtain a plurality of downsampled fixed images 141 as the training data for the model training module 200, wherein the plurality of downsampled fixed images 141 are downsampled from the plurality of fixed images 111 by NUFFT for simulating the dynamic images in real-time tracking and MR image acquisition as input to a deformable registration network. The plurality of downsampled fixed images 141 at different moments are combined and linked together to form the corresponding downsampled 4D MR image 140 of the 4D MR image 110. In addition, for enhancing the accuracy and providing retrospective data, a reference DVF 160 is computed from the 4D MR image 110 using conventional registration methods as ground truth DVF for supervising the model training module 200. In certain embodiments, the conventional registration methods may comprise a parametric total variation (pTV) algorithm.

Alternatively, the k-space data 120 may be used directly as the training data for the model training module 200. In such case, a complex neural network is used to directly reconstruct the collected k-space data 120 without iNUFFT. This alternative configuration can improve the quality of the training data and further improve the accuracy of the training model.

Figure 3:
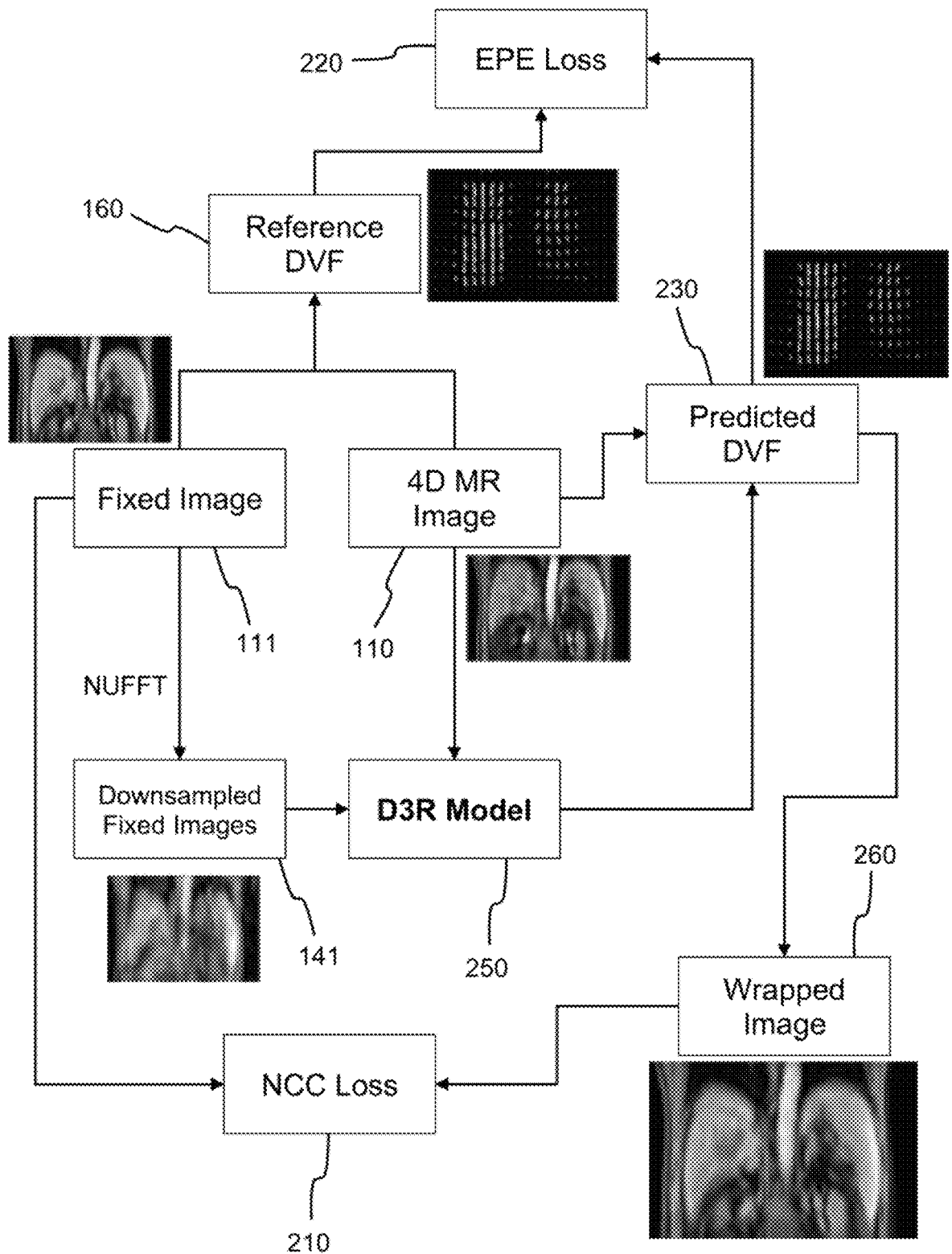
FIG. 3 shows a block diagram of the model training module in accordance with certain embodiments of the present disclosure.

FIG. 3 shows a block diagram of the model training module 200, which is used to perform deformation registration of the corresponding downsampled 4D MR image 140 to train a deep learning-based model by a machine learning method with respect to a pair of original and downsampled 4D MRI data, in accordance with certain embodiments of the present disclosure. The training data for the model training module 200 comprises the 4D MR image 110 and the corresponding downsampled 4D MR image 140 from the data pre-processing module 100. The model training module 200 comprises a CNN 250, which is trained to calculate a predicted DVF 230. Although CNN is applied in the present disclosure, it is apparent that other deep learning-based models may be used. The performance of the CNN 250 is highly dependent on the training data, which is obtained from different medical institutes and different MRI apparatuses. With training data from a considerable number of patients of different medical institutes, the model training module 200 can achieve better generalization for fine-tuning the CNN 250. In one preferred embodiment, the CNN 250 is a dual-supervised downsampling-invariant deformable registration (D3R) model. Since the real-time tracking requires an imaging frequency greater than 3 Hz and the repetition time (TR) in the T1w MRI sequence is around 3 ms, 100 radial spokes 130 are utilized to reconstruct the training images. The model training module 200 is dually supervised with two kinds of reference data. In the preferred embodiment, the model training module 200 is supervised by the end-to-end point error (EPE) 220 and the normalized correlation coefficient (NCC) 210. In certain embodiments, the EPE 220 determines a first loss function between the reference DVF 160 (ground truth DVF) and the predicted DVF 230, while the NCC 210 determines a second loss function between the warped image 260 and the 4D MR image 110. The first and second loss functions are used for supervising the training of the CNN 250.

Figure 4:
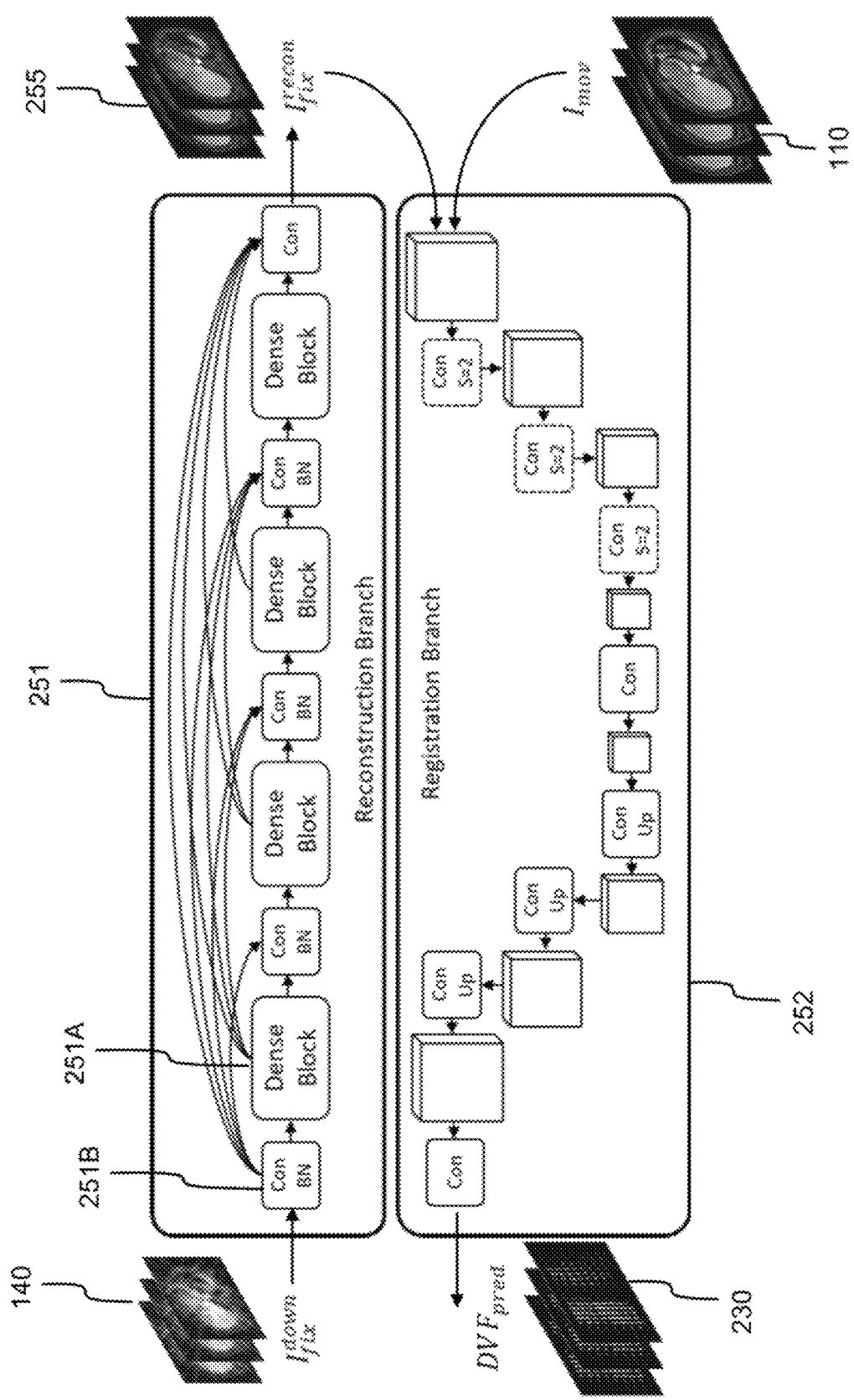
FIG. 4 shows the network architecture of the dual-supervised downsampling-invariant deformable registration (D3R) model in accordance with certain embodiments of the present disclosure.

FIG. 4 shows the network architecture of the D3R model, which is the preferred embodiment of the CNN 250, in accordance with certain embodiments of the present disclosure. The D3R model comprises a reconstruction branch 251 and a registration branch 252. The reconstruction branch 251 is configured to reconstruct the plurality of downsampled fixed images 140 using a densely connected network to obtain reconstructed fixed images 255. In certain embodiments, the densely connected network may be the Dense Convolutional Network (DenseNet) [4] having a plurality of layers each having a dense block 251A and a transition layer 251B. In particular, an individual layer receives inputs from outputs of all previous layers of the plurality of layers, and the transition layer 251B is configured to perform convolution and pooling. The densely connected network features a feed-forward characteristic for enhancing the image details and suppressing the artifacts.

The reconstructed fixed images 255 and the 4D MR image 110 are received by the registration branch 252 to predict the deformations between them, thereby the registration branch 255 generates the predicted DVF 230 for the image generation module 300. In certain embodiments, the registration branch 252 is a supervised registration framework based on the CNN 250, which is configured to determine the predicted DVF 230 between two frames of images. For example, the registration branch 252 may be based on any medical image registration techniques, such as the VoxelMorph [5]. The reconstructed fixed images 255 and the 4D MR image 110 are paired and mapped as a DVF pair for alignment. Throughout the training process, the reconstruction loss and the registration loss are dually supervised. The previous data from the data pre-processing module 100 are fed into the D3R model for training. The training of the reconstruction branch 251 is supervised with the 4D MR image 110, and the training of the registration branch 252 is supervised with image similarity and a pre-prepared reference DVF 160. The 4D MR image 110 only needs one frame whose respiratory phase matches fixed image 111, which is called a representative frame. Image segmentation and registration are further performed to deformably register the representative frame with the fixed image 111 for eliminating possible bias. Afterwards, the D3R model is used to deform-register the representative frame with all frames of downsampled fixed images 141 in the corresponding downsampled 4D MR image 140 to obtain the predicted DVF 230 from the representative frame to each frame. After training to convergence, a trained CNN 250 is obtained.

Figure 5:
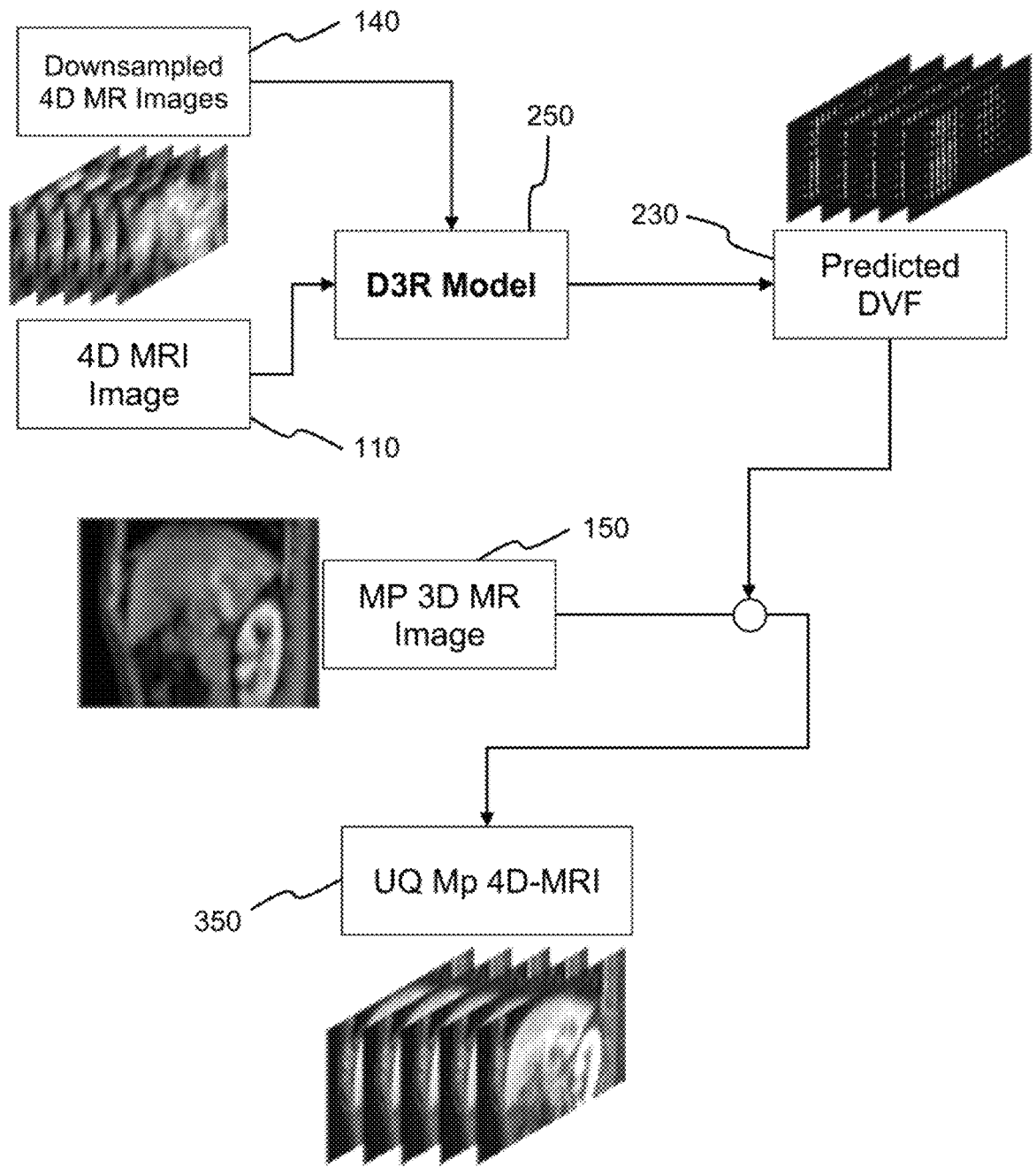
FIG. 5 shows a block diagram of the image generation module in accordance with certain embodiments of the present disclosure.

FIG. 5 shows a block diagram of the image generation module 300 for estimating the multi-parametric 4D MR image 350 in accordance with certain embodiments of the present disclosure. The image generation module 300 may be programmed as a software executed by the processor of the one or more computer devices. In particular, the multi-parametric 4D MR image 350 is a UQ Mp 4D MR image. Advantageously, the use of the multi-parametric 3D MR images 150 can simply the multiple scans of 4D MR image to a signal scan, which can reduce the financial burden on the patients and improve treatment efficiency for the hospitals. In certain embodiments, the image generation module 300 receives the predicted DVF 230 from the trained CNN 250, and the multi-parametric 3D MR images 150 for estimating the multi-parametric 4D MR image 350. In particular, the predicted DVF 230 obtained from the CNN 250 is used to deform the multi-parametric 3D MR images 150 to estimate the multi-parametric 4D MR image 350 in real-time.

The registration performance and robustness of the D3R model are compared to conventional methods, including Demons, Elastix, and pTV algorithm. The constructed multi-parametric 4D MR image 350 is evaluated by tumor tracking accuracy and image quality indicators, including tumor contrast-to-noise ratio (CNR), liver-lung edge sharpness, and perceptual blur metric (PBM). The D3R model shows significantly higher image similarity measures than other conventional methods.

Figure 6:
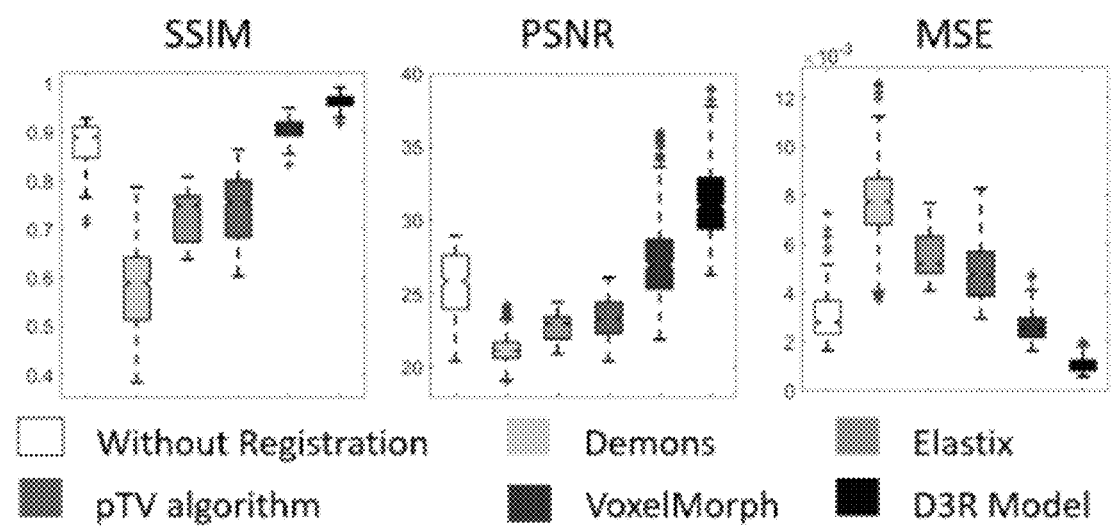
FIG. 6 shows the comparison between D3R model and other conventional methods on the structure similarity index measure (SSIM), peak signal-to-noise ratio (PSNR), and mean squared error (MSE)

For the registration between original 4D MR image 110 and the plurality of downsampled fixed images 141, the D3R model shows significantly smaller mean squared error (MSE), and higher peak signal-to-noise ratio (PSNR) and structure similarity index measure (SSIM) than all the conventional methods ($p<0.001$ for all metrics). The comparison is summarized in FIG. 6. D3R model shows significantly improve quantitative metrics, which is more robust to downsampling artifacts with better organ alignment. In particular, the multi-parametric 4D MR image 350 obtained from the present invention has an improved tumor CNR, an improved organ edges sharpness, and a reduced PBM.

Figure 7:
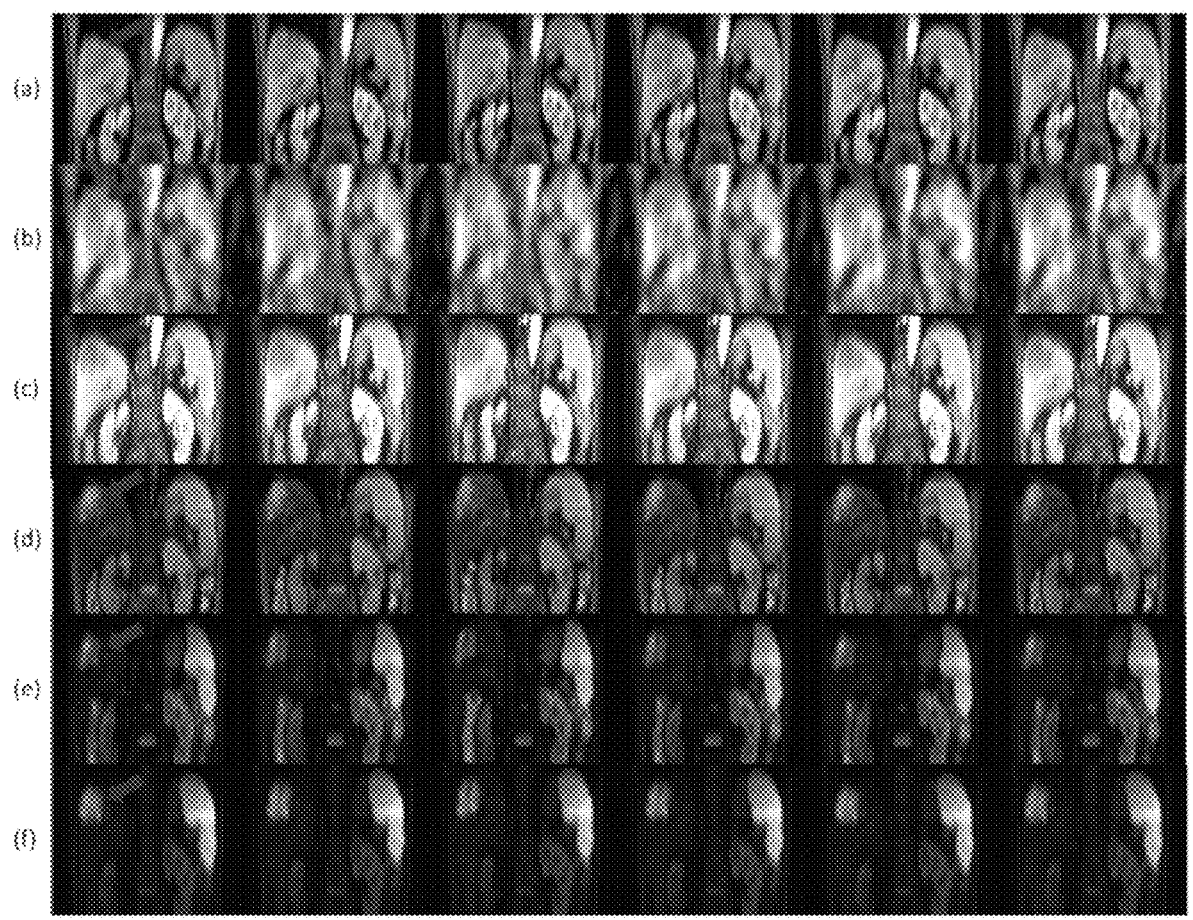
FIG. 7 shows the 4D MR image and the multi-parametric 4D MR image in the coronal view of an exemplary patient.

To visually illustrate the performance, the 4D MR image 110 and the multi-parametric 4D MR image 350 in the coronal view of an exemplary patient is shown in FIG. 7. In the figure, the original 4D MR image 110 is shown in row (a). The corresponding downsampled 4D MR image 140 is shown in row (b). The multi-parametric 4D MR image 350 is shown in rows (c) to (f). In particular, row (c) refers to the T1w, row (d) refers to the T2w, row € refers to the DWI with b=50, and row (f) refers to the DWI with b=800. The tumor contrast is significantly improved in the T1w and T2w images.

Figure 8:
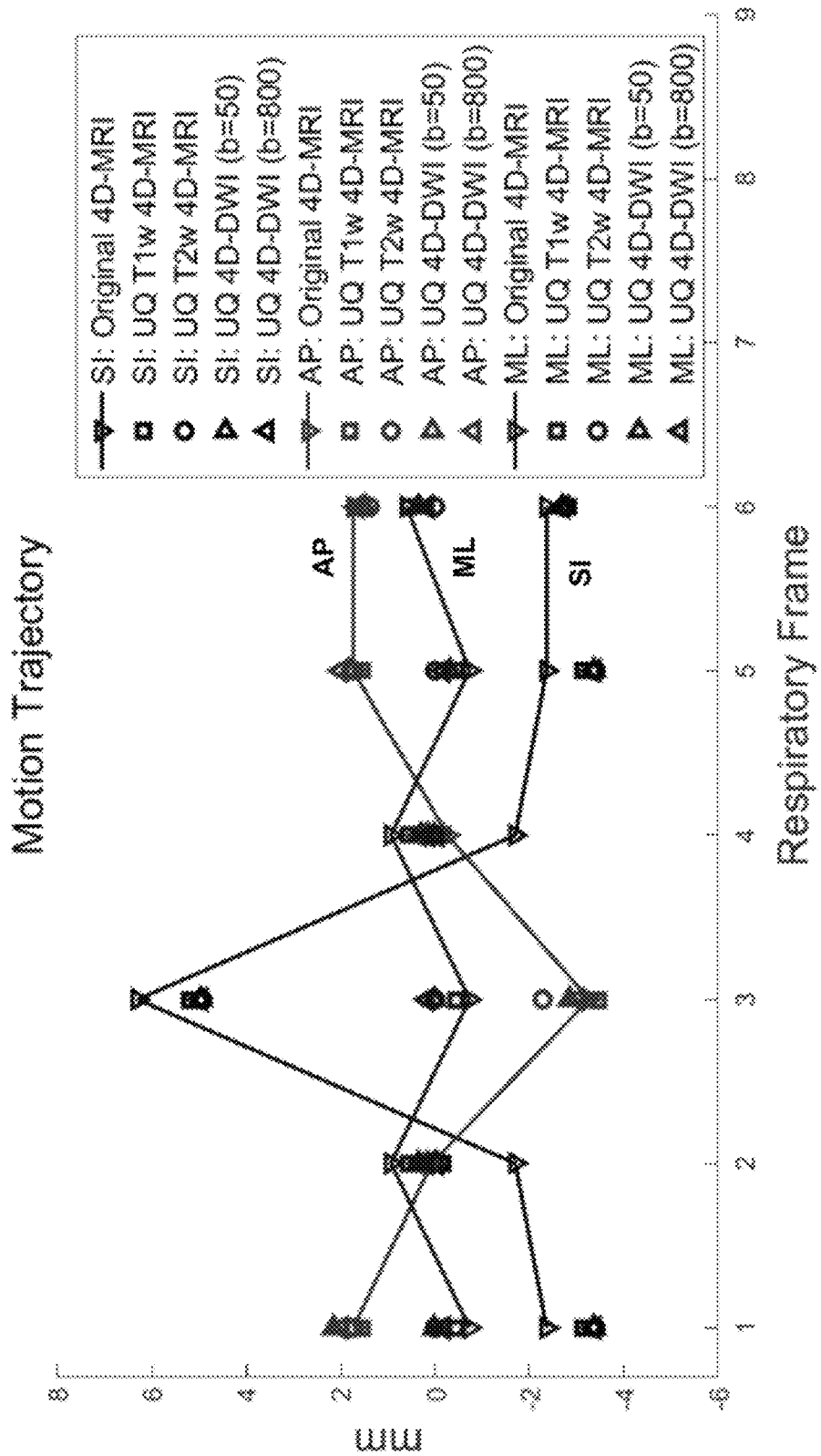
FIG. 8 shows the tumor motion trajectories of the same patient of FIG. 7.

FIG. 8 shows the corresponding tumor motion trajectories of the same patient as that in FIG. 7. In the presented six consecutive frames, the image quality of the corresponding downsampled 4D MR image 140 is greatly degraded, and the anatomical structures are difficult to identify. In comparison, the constructed multi-parametric 4D MR image 350 exhibits better defined anatomical boundaries with greatly improved tumor contrast. Therefore, the tumor motion can be accurately reflected in the multi-parametric 4D MR image 350, with a maximum error of less than 2 mm. The organ motions, including those caused by the reflecting respiratory movement, can well-matched with the original 4D MR image 110.

Further statistical results from 31 patients with liver tumor are listed in FIG. 9. The 4D MR image 110 is obtained using TWIST volumetric interpolated breath-hold examination (TWIST-VIBE) sequence. In the table, the multi-parametric 4D MR image 350 shows significantly improved image quality and accurate tumor motion trajectory compared to the original 4D MR image 110. The relative tumor motion errors are 1.18±1.20, 0.52±0.55, and 0.41±0.47 mm in the superior-inferior, anterior-posterior, and mid-lateral directions. From the original 4D MR image 110 to the multi-parametric 4D MR image 350, CNR increased from 8.30±6.87 to 35.28±35.29, lung-liver edge full-width-at-half-maximum decreased from 8.7±6.4 mm to 5.2±2.4 mm, and PBM decreased from 0.70±0.01 to 0.38±0.01. The result demonstrates promising results for real-time tumor tracking in liver radiation therapy.

This illustrates the fundamental 4D MRI system and method for generating real-time ultra-quality multi-parametric 4D MR images in accordance with the present disclosure. It will be apparent that variants of the above-disclosed and other features and functions, or alternatives thereof, may be combined into many other different kinds of medical devices for performing radiotherapy on various internal organs. The present embodiment is, therefore, to be considered in all respects as illustrative and not restrictive. The scope of the disclosure is indicated by the appended claims rather than by the preceding description, and all changes that come within the meaning and range of equivalency of the claims are therefore intended to be embraced therein.

CITED REFERENCES

The following documents are cited in this patent application. References [1]-[5] are incorporated by reference herein.

[1] Li G, Wei J, Kadbi M, et al. Novel Super-Resolution Approach to Time-Resolved Volumetric 4-Dimensional Magnetic Resonance Imaging with High Spatiotemporal Resolution for Multi-Breathing Cycle Motion Assessment. *International journal of radiation oncology, biology, physics*. 2017;98(2):454-462. doi:10.1016/j.ijrobp.2017.02.016.

[2] Freedman J N, Collins D J, Gurney-Champion O J, et al. Super-resolution T2-weighted 4D MRI for image guided radiotherapy. *Radiother Oncol*. December 2018;129(3):486-493. doi:10.1016/j.radonc.2018.05.015.

[3] Zhang L, Yin F F, Li T, et al. Multi-contrast four-dimensional magnetic resonance imaging (MC-4D-MRI): Development and initial evaluation in liver tumor patients. *Med Phys*. December 2021;48(12):7984-7997. doi:10.1002/mp.15314.

[4] Huang G, Liu Z, Van Der Maaten L, Weinberger K Q. Densely connected convolutional networks. 2017:4700-4708.

[5] Balakrishnan G, Zhao A, Sabuncu M R, Guttag J, Dalca A V. VoxelMorph: a learning framework for deformable medical image registration. *IEEE Trans Med Imaging*. Feb. 4, 2019;doi:10.1109/TMI.2019.2897538

What is claimed is:

1. A computer-implemented method for training a convolutional neural network (CNN) using training data comprising a pair of original and downsampled 4D magnetic resonance imaging (MRI) data, the CNN used to generate multi-parametric 4D magnetic resonance (MR) images based on multi-parametric 3D MR images in real-time, the multi-parametric 4D MR images having an improved tumor contrast-to-noise ratio (CNR), an improved organ edges sharpness, and a reduced perceptual blur metric (PBM), the method comprising:

receiving, by a processor, a 4D MR image formed by a plurality of fixed images of different frames;

converting, by the processor, the plurality of fixed images into a plurality of k-space data by non-uniform fast Fourier transform (NUFFT), wherein the plurality of k-space data is an array of numbers representing spatial frequencies of the plurality of fixed images in a Cartesian coordinate system;

applying, by the processor, radial scan to the plurality of k-space data to simulate real-time MR image acquisition; and generating a plurality of downsampled fixed images by inverse NUFFT (iNUFFT) for forming a corresponding downsampled 4D MR image;

reconstructing, by the processor, the plurality of downsampled fixed images using a densely connected network in a reconstruction branch of a dual-supervised downsampling-invariant deformable registration (D3R) model to obtain reconstructed fixed images with enhanced image details and suppressed artifacts;

training, by a machine learning method, the CNN with training data comprising the 4D MR image and the corresponding downsampled 4D MR image and the reconstructed fixed images, wherein the CNN is the D3R model comprising the reconstruction branch and a registration branch and is trained to calculate a predicted displacement vector field (DVF) based on deformable registration of the reconstructed fixed images and the 4D MR image by the registration branch; and estimating, by the processor, the multi-parametric 4D MR image in real-time by applying the predicted DVF to the multi-parametric 3D MR images.

2. The method of claim 1 further comprising dually supervising the step of training the CNN by an end-to-end point error (EPE) and a normalized correlation coefficient (NCC).

3. The method of claim 2 further comprising generating a reference DVF from the 4D MR image using conventional registration methods as a ground truth DVF, wherein the conventional registration methods comprise a parametric total variation (pTV) algorithm.

4. The method of claim 3, wherein the step of dually supervising the step of training the CNN further comprises determining a first loss function between the reference DVF and the predicted DVF as the EPE; and determining a second loss function between a warped image and the 4D MR image as the NCC.

5. The method of claim 1, wherein the step of training the CNN comprises:

deformably registering, by the registration branch, the reconstructed fixed images and the 4D MR image to predict deformations between the reconstructed fixed images and the 4D MR image for determining the predicted DVF.

6. The method of claim 5, wherein:

the densely connected network comprises a plurality of layers each having a dense block and a transition layer; and an individual layer receives inputs from outputs of all previous layers of the plurality of layers.

7. The method of claim 6, wherein the step of reconstructing the plurality of downsampled fixed images further comprises performing convolution and pooling, wherein the densely connected network is characterized with a feed-forward characteristic for enhancing image details and suppressing artifacts.

8. The method of claim 5, wherein the step of deformably registering the reconstructed fixed image and the 4D MR image further comprises pairing and mapping the reconstructed fixed image and the 4D MR image to a DVF pair for alignment, wherein the registration branch is a supervised registration framework based on the CNN.

9. The method of claim 1, wherein the multi-parametric 3D MR images comprise T1-weighted (T1w) MRI, T2-weighted (T2w) MRI, and diffusion-weighted MR imaging (DWI).

10. A four-dimensional (4D) magnetic resonance imaging (MRI) system for generating multi-parametric 4D magnetic resonance (MR) images based on multi-parametric 3D MR images in real-time, the multi-parametric 4D MR images having an improved tumor contrast-to-noise ratio (CNR), an improved organ edges sharpness, and a reduced perceptual blur metric (PBM), the system comprising:

one or more computer devices collectively programmed with a data pre-processing module, a model training module, and an image generating module, wherein:

the data pre-processing module is configured to downsample a 4D MR image by non-uniform fast Fourier transform (NUFFT) and generate a corresponding downsampled 4D MR image, wherein:

the 4D MR image is formed by a plurality of fixed images of different frames, the plurality of fixed images are converted into a plurality of k-space data by the non-uniform fast Fourier transform (NUFFT), the plurality of k-space data is an array of numbers representing spatial frequencies of the plurality of fixed images in a Cartesian coordinate system, radial scan is applied to the plurality of k-space data to simulate real-time MR image acquisition, and a plurality of downsampled fixed images are generated by inverse NUFFT (iNUFFT) for forming the corresponding downsampled 4D MR image;

the data pre-processing module is further configured to reconstruct the plurality of downsampled fixed images using a densely connected network in a reconstruction branch of a dual-supervised downsampling-invariant deformable registration (D3R) model to obtain reconstructed fixed images with enhanced image details and suppressed artifacts;

the model training module is configured to train a convolutional neural network (CNN) with training data using a machine learning method, wherein the CNN is the D3R model comprising the reconstruction branch and a registration branch, the training data comprises the 4D MR image, the corresponding downsampled 4D MR image and the reconstructed fixed images from the data pre-processing module, and the CNN is trained to calculate a predicted displacement vector field (DVF) based on deformable registration of the reconstructed fixed images and the 4D MR image by the registration branch; and the image generation module is configured to apply the predicted DVF to the multi-parametric 3D MR images to estimate the multi-parametric 4D MR image in real-time, wherein:

the training data for the CNN comprises the 4D MR image and the corresponding downsampled 4D MR image from the data pre-processing module;

the model training module is dually supervised by an end-to-end point error (EPE) and a normalized correlation coefficient (NCC); and the model training module is configured to perform deformation registration of the corresponding downsampled 4D MR image to train the CNN.

11. The system of claim 10, wherein the 4D MR image is a moving image formed by the plurality of fixed images.

12. The system of claim 10, wherein the reconstruction branch is configured to reconstruct the plurality of downsampled fixed images using a densely connected network to obtain reconstructed fixed images, wherein:

the densely connected network comprises a plurality of layers each having a dense block and a transition layer; and an individual layer receives inputs from outputs of all previous layers of the plurality of layers.

13. The system of claim 12, wherein the transition layer is configured to perform convolution and pooling; and the densely connected network is characterized with a feed-forward characteristic for enhancing image details and suppressing artifacts.

14. The system of claim 12, wherein the registration branch receives the reconstructed fixed images and the 4D MR image for predicting deformations between the reconstructed fixed images and the 4D MR image, thereby the registration branch generates the predicted DVF for the image generation module.

15. The system of claim 14, wherein the registration branch is a supervised registration framework based on the CNN, wherein the reconstructed fixed images and the 4D MR image are paired and mapped to a DVF pair for alignment.

16. The system of claim 10, wherein the EPE determines a first loss function between a reference DVF and the predicted DVF; and the NCC determines a second loss function between a warped image and the 4D MR image.

17. The system of claim 16, wherein the reference DVF is a ground truth DVF computed from the 4D MR image using conventional registration methods for supervising the model training module, wherein the conventional registration methods comprise a parametric total variation (pTV) algorithm.

* * * * *